United States Patent [19]

Gonzalez, Jr.

[11] Patent Number: 5,599,561

[45] Date of Patent: Feb. 4, 1997

[54] METHOD OF MAKING POULTICE

[76] Inventor: Angel Gonzalez, Jr., P.O. Box 211, Peterborough, N.H. 03458

[21] Appl. No.: 511,460

[22] Filed: Aug. 4, 1995

[51] Int. Cl.$^6$ .......... A61K 31/05; A61K 31/055; A61K 33/06; A61K 33/18

[52] U.S. Cl. .......... 424/670; 424/667; 424/669; 424/682; 424/684; 424/696; 424/697; 424/195.1; 514/557; 514/729; 514/731; 514/737; 514/783; 514/969

[58] Field of Search .......... 424/670, 667, 424/669, 682, 684, 696, 697, 195.1; 514/557, 729, 731, 737, 783, 969

[56] References Cited

U.S. PATENT DOCUMENTS

| | | | |
|---|---|---|---|
| 40,189 | 10/1863 | Scott | 424/195.1 |
| 308,243 | 11/1884 | Elberson | 424/196.1 |
| 350,405 | 10/1886 | Wyeth | 424/195.1 |
| 359,611 | 3/1887 | Jones | 424/697 |
| 1,519,755 | 12/1924 | Chapman | 424/195.1 |
| 2,409,959 | 5/1947 | Brown | 424/195.1 |
| 3,698,392 | 10/1972 | Vogt et al. | 604/304 |
| 3,780,537 | 12/1973 | Spencer | 62/530 |
| 4,352,796 | 10/1982 | Arichi et al. | 424/195.1 |
| 4,483,716 | 11/1984 | Heller | 134/7 |
| 5,248,503 | 9/1993 | Emanuel-King | 424/195.1 |
| 5,476,492 | 12/1995 | Unrug | 607/114 |
| 5,512,278 | 4/1996 | Mundschenk | 514/900 |

OTHER PUBLICATIONS

Remington's Pharmaceutical Sciences, 18th ed., Easton, PA, Mack Printing Co., 1990, pp. 763 and 1613.

Bennett, H. (ed.), The Chemical Formulary, NY, Chemical Publishing Co., Inc., 1941, vol. V, p. 70.

Martindale The Extra Pharmacopoeia, 13th ed., London, The Pharmaceutical Press, 1993, pp. 857–858.

*Primary Examiner*—John Pak
*Attorney, Agent, or Firm*—George W. Dishong

[57] ABSTRACT

A method of making poultice by mixing together water, fine mineral powder, vinegar, herbal liniment solution, and hydrated magnesium sulfate (also known as Epsom salt) to produce a poultice capable of being applied to muscles, joints, or both which may be sore, injured, or both.

14 Claims, No Drawings

METHOD OF MAKING POULTICE

FIELD OF THE INVENTION

The present invention relates generally to poultices and the method of making thereof; and more particularly to a method of making a poultice which sooths and accelerates the healing process of sore and injured muscles and joints.

BACKGROUND

Muscles and joints can become sore or injured in many different ways. A frequent cause of soreness and injury to muscles and joints is athletic or other physical activity. Injured or sore muscles and joints can hinder athletic and physical performance and can be painful.

In the past, poultices have proven effective for soothing and helping to acclerate the healing process of sore or injured muscles and joints. While poultices can be used on a wide variety of creatures, including humans, poultices have been particularly useful on horses. Even more particulary, poultices can be used in the horse racing and training industry to reduce the hindrance of the horses physical and athletic performance due to injury or soreness of the horses muscles and joints. Such poultices are similarly useful on any work animal, such as a horse, dog, oxen, mule, donkey, or bull.

The primary reasons poultices are used, in treating sore or injured muscles and joints are to accelerate the healing process, and to reduce the pain associated with the soreness or injury. It is thus desirable to have a method of making a poultice which is capable of accelerating the healing process and reducing the amount of pain associated with the injury or soreness.

For the foregoing reasons, there is a need for a method of making a poultice that is capable of reducing the pain associated with sore or injured muscles and joints and that reduces the hindrance to athletic and other physical activity due to sore or injured muscles and joints.

SUMMARY OF THE INVENTION

The present invention is directed to a method of making poultice that satisfies the needs of producing a poultice which is capable of reducing the pain associated with sore or injured muscles and joints and that reduces the hindrance to athletic and other physical activity due to sore or injured muscles and joints. A method of making poultice having features of the present invention comprises mixing water with vinegar, herbal liniment solution, hydrated magnesium sulfate (also known as Epsom salt), and fine mineral powder.

A primary object of the present invention is to provide a method of making a poultice that is capable of reducing the pain associated with sore or injured muscles and joints and that reduces the hindrance to athletic and other physical activity due to sore or injured muscles and joints.

Another primary object of the present invention is to provide a method of making a poultice that, when stored in a sealed container will have a shelf life of more than one year.

Yet another primary object of the present invention is to provide a method of making a poultice that will not be substantially damaged if frozen during storage.

An object of the present invention is to provide a method for making poultice which poultice has at least water, vinegar, herbal liniment, hydrated magnesium sulfate and a fine mineral powder. The method provides for the steps of putting, into a container, preferably a mixer such as a cement mixer, water which is preferably potable water, vinegar which is preferably cider vinegar, herbal liniment such as ABSORBINE® brand of herbal liniment, hydrated magnesium sulfate sometimes known as "Epsom salt", a fine mineral powder such as for example wherein said fine mineral powder may be comprised of kaolinite and quartz and which may be Hydrous Aluminum Silicate or Ball Clay and preferable the fine mineral powder is a clay sold under the trademark "BOWIE CLAY PLUS" and mixing the materials in the container until the mixture is properly textured, has the desired consistency and is substantially free of lumps producing thereby the poultice.

Another object of the present invention is to provide the poultice according to the above method wherein the amounts of each of the materials relative to about 200 pounds of fine mineral powder is given in the approximate amounts of about: 7 gallons of water; about 2.5 gallons of vinegar; about ⅓ gallon of herbal liniment solution; and about 6 quarts hydrated magnesium sulfate.

Yet another object of the present invention is to make the poultice in successive stages of mixture. Making a first mixture using the steps of; putting into a mixer about 7 gallons of water about 1 gallon cider vinegar, about ⅓ gallon herbal liniment solution, adding about 3 quarts of hydrated magnesium sulfate, and mixing, thereby making the first mixture. A second mixture is made using the first mixture and adding the steps of adding; a first about 50 pounds of fine mineral powder, mixing for about 10 minutes, thereby making the second mixture. A third mixture is made using the second mixture and adding the steps of adding; a second about 50 pounds of fine mineral powder, about ½ gallon cider vinegar, mixing for about 10 minutes, thereby making the third mixture. A fourth mixture is made using the third mixture and adding the steps of adding; about 25 pounds of fine mineral powder, mixing for about 5 minutes thereby making the fourth mixture. A fifth mixture is made using the fourth mixture and adding the steps of adding; about 15 pounds of fine mineral powder, about ½ gallon cider vinegar, about 3 quarts of hydrated magnesium sulfate, mixing for about 10 minutes thereby making the fifth mixture. A sixth mixture is made using the fifth mixture and adding the steps of adding; about 10 pounds of fine mineral powder, mixing the about 10 pounds of fine mineral powder and the fifth mixture until the mixture is smooth, thereby making the sixth mixture. And a seventh mixture is made using the sixth mixture and adding the steps of adding; about ½ gallon of cider vinegar, adding a third about 50 pounds of fine mineral powder incrementally during one hour while mixing the about ½ gallon of cider vinegar and the sixth mixture, thereby making the seventh mixture. The seventh mixture being the poultice having the desired consistency and character.

These and further objects of the present invention will become apparent to those skilled in the art after a study of the present disclosure of the invention.

DESCRIPTION OF THE PREFERRED EMBODIMENT

A method according to the present invention for making poultice comprises the following steps of mixing together water, vinegar, herbal liniment solution, and hydrated magnesium sulfate, (also known as Epsom salt); adding fine mineral powder. For best results, it is preferred that the water used be potable. Further, it is preferred that the vinegar used be cider vinegar.

While many different herbal liniment solutions may be used, the preferred herbal liniment solution includes as ingredients: acetone, iodine, potassium iodide, menthol, thymol, and chloroxylenol. Further, an example of a desireable herbal liniment solution is a veterinary liniment sold under the trademark "ABSORBINE".

Regarding the fine mineral powder, there are several which will suffice, namely: Clay, Ball Clay, Hydrous Aluminum Silicate, AL2O3.2SIO2.2H2O+impurities, or a composition of at least 70% by weight Kaolinite and no more than 30% by weight Quartz. Additionally, fine mineral powders sold under the trademarks "OLD HICKORY CLAY" or "POULTICE POWDER" will suffice. The preferred fine mineral powder is a clay sold under the trademark "BOWIE CLAY PLUS" aviable from Muel-Fol Company Inc. located in New Milford, N.J. "BOWIE CLAY PLUS" is a hydrous aluminum silicate with a chemical formula of $AL_2O_3 \cdot 2SIO_2 \cdot 2H_2O$+impurities.

The poultice ingredients are preferably mixed in such a way that the resulting poultice has a consistency making it easily spreadable over the affected area of the body and a consistency such that the poultice will substantially stay where it is spread. An example of a desireable consistency of the poultice which will facilitate spreading is that of peanut butter spread at room temperature. Another example of the consistency is that of brick mortar. These and other features, aspects, and advantages of the present invention will become better understood with reference to the following description and the appended claims.

In the preferred embodiment of this invention, it is desirable to make the poultice in batches of about 300–350 pounds each. A batch size of about 300–350 pounds allows for the poultice to be conveniently mixed using a conventional cement mixer.

A cement mixer is preferably used as the mixer of the present invention, although, the method of the present invention can performed using any container of sufficient size to contain the material being mixed. To obtain superior mixing, the cement mixer should be operated in a clockwise direction rather than the counterclockwise direction normally used for mixing cement. Operating the conventional cement mixer in a clockwise direction causes the material being mixed to be mixed by a pushing-away action by the mixing blades within the mixer. Additionally, to make the mixing more vigorous, the cement mixer may be tilted away from vertical. The more horizontal the cement mixer, the more vigorous the mixing within.

One embodiment of the present invention for method of making poultice is made by the following steps:

The first step includes, making a first mixture by putting 7 gallons of water into a mixer, putting 1 gallon cider vinegar into the mixer, putting ⅓ gallon herbal liniment solution into the mixer, adding 3 quarts of hydrated magnesium sulfate into the mixer, mixing in the mixer the 7 gallons of water, the 1 gallon cider vinegar, the ⅓ gallon herbal liniment solution, and the 3 quarts of hydrated magnesium sulfate, until the 3 quarts of hydrated magnesium sulfate is substantially dissolved, thereby making the first mixture The second step includes, making a second mixture by adding to the first mixture 50 pounds of fine mineral powder, mixing for about about 10 minutes in the mixer the first mixture and the 50 pounds of fine mineral powder, thereby making the second mixture.

The third step includes, making a third mixture by adding a second 50 pounds of fine mineral powder to the second mixture, adding ½ gallon cider vinegar to the second mixture, and mixing for about 10 minutes in the mixer the second mixture, the ½ gallon cider vinegar, and the second 50 pounds of fine mineral powder, thereby making the third mixture.

The fourth step includes, making a fourth mixture by adding about 25 pounds of fine mineral powder to the third mixture, and mixing for about 5 minutes in the mixer the 25 pounds of fine mineral powder and said third mixture, thereby making said fourth mixture.

The fifth step includes, making a fifth mixture by adding 15 pounds of fine mineral powder to the fourth mixture, adding ½ gallon cider vinegar to the fourth mixture, adding 3 quarts of hydrated magnesium sulfate to the fourth mixture, and mixing for about 10 minutes in the mixer the 15 pounds of fine mineral powder, the ½ gallon cider vinegar, the 3 quarts of hydrated magnesium sulfate, and the fourth mixture, thereby making the fifth mixture.

The sixth step includes making a sixth mixture by adding 10 pounds of fine mineral powder to the fifth mixture, mixing the 10 pounds of fine mineral powder and the fifth mixture until the mixture of the 10 pounds of fine mineral powder and the fifth mixture is smooth, thereby making said sixth mixture.

The seventh step includes making a seventh mixture by adding ½ gallon of cider vinegar to the sixth mixture, adding a third 50 pounds of fine mineral powder incrimentally during one hour while mixing the ½ gallon of cider vinegar and the sixth mixture, thereby making the seventh mixture.

The mixing times associated with the various mixing steps can be as little as two minutes per step. While there is no set upper limit on how long a mixing step should last, for efficiency, the upper limit should not exceed about 20 minutes except in the seventh step where mixing times up to 2 hours are acceptable.

In order to achive the preferred consistency and the preferred results of the poultice made by the method of this invention, several preferred ratios of ingredients may be employed. The prefered ratio of water to fine mineral powder is about 7 gallons of water to about 200 pounds of fine mineral powder. The preferred ratio of vinegar to fine mineral powder is about 2.5 gallons of vinegar to about 200 pounds of fine mineral powder. The preferred ratio of herbal liniment solution to fine mineral powder is about ⅓ gallon of herbal liniment solution to about 200 pounds of fine mineral powder. The preferred ratio of hydrated magnesium sulfate (also known as Epsom salt) to fine mineral powder is about 6 quarts hydrated magnesium sulfate to about 200 pounds of fine mineral powder.

It is thought that many of the attendant advantages of the present invention will be understood from the foregoing description and it will be apparent that various changes may be made in the composition and materials and method used without departing from the spirit and scope of the invention or sacrificing all of its material advantages, the form hereinbefore described being merely a preferred or exemplary embodiment thereof.

I claim:

1. A method of making poultice, which comprises:

adding water into a container;

adding vinegar into said container;

adding an herbal liniment solution comprising acetone, iodine, potassium iodide, menthol, thymol and chloroxylenol into said container;

adding hydrated magnesium sulfate into said container;

adding a fine mineral powder selected from the group consisting of clay, hydrous aluminum silicate, and a mixture of kaolinite and quartz, into said container; and mixing said water, said vinegar, said herbal liniment solution, said hydrated magnesium sulfate, and said fine mineral powder to spreadable consistency.

2. The method of claim 1, wherein said fine mineral powder is clay.

3. The method of claim 2, wherein said clay is ball clay.

4. The method of claim 1, wherein said fine mineral powder is hydrous aluminum silicate.

5. The method of claim 1, wherein said fine mineral powder is a mixture of kaolinite and quartz.

6. The method of claim 1, wherein said water is potable water.

7. The method of claim 1, wherein said vinegar is cider vinegar.

8. The method of claim 1 wherein said container is a mixer.

9. The method of claim 8 wherein said mixer is a cement mixer.

10. The method of claim 1 wherein the ratio of water to fine mineral powder is about 7 gallons of water to 200 pounds fine mineral powder.

11. The method of claim 1 wherein the ratio of vinegar to fine mineral powder is about 2.5 gallons of vinegar to 200 pounds fine mineral powder.

12. The method of claim 1 wherein the ratio of herbal liniment solution to fine mineral powder is about ⅓ gallon of herbal liniment solution to 200 pounds fine mineral powder.

13. The method of claim 1 wherein the ratio of hydrated magnesium sulfate to fine mineral powder is about 6 quarts hydrated magnesium sulfate to 200 pounds fine mineral powder.

14. A method of making poultice comprising:

making a first mixture, said making a first mixture comprising the steps:
adding about 7 gallons of water into a mixer,
adding about 1 gallon cider vinegar into said mixer,
adding about ⅓ gallon herbal liniment solution comprising acetone, iodine, potassium iodide, menthol, thymol and chloroxylenol into said mixer,
adding about 3 quarts of hydrated magnesium sulfate into said mixer,
mixing in said mixer said about 7 gallons of water, said about 1 gallon cider vinegar, said about ⅓ gallon herbal liniment solution, and said about 3 quarts of hydrated magnesium sulfate, until said about 3 quarts of hydrated magnesium sulfate is substantially dissolved, thereby making said first mixture;

making a second mixture, said making a second mixture comprising the steps:
adding to said first mixture a first about 50 pounds of fine mineral powder, selected from the group consisting of clay, hydrous aluminum silicate, and a mixture of koalinite and quartz,
mixing for about 10 minutes in said mixer said first mixture with said first about 50 pounds of fine mineral powder thereby making said second mixture;

making a third mixture, said making a third mixture comprising the steps:
adding a second about 50 pounds of fine mineral powder selected from the group consisting of clay, hydrous aluminum silicate, and a mixture of kaolinite and quartz to said second mixture,
adding about ½ gallon cider vinegar to said second mixture,
mixing for about 10 minutes in said mixer said second mixture, said about ½ gallon cider vinegar, and said second about 50 pounds of fine mineral powder thereby making said third mixture;

making a fourth mixture, said making a fourth mixture comprising the steps:
adding about 25 pounds of fine mineral powder selected from the group consisting of clay, hydrous aluminum silicate, and a mixture of kaolinite and quartz to said third mixture,
mixing for about 5 minutes in said mixer said about 25 pounds of fine mineral powder and said third mixture thereby making said fourth mixture;

making a fifth mixture, said making a fifth mixture comprising the steps:
adding about 15 pounds of fine mineral powder selected from the group consisting of clay, hydrous aluminum silicate, and a mixture of kaolinite and quartz to said fourth mixture,
adding about ½ gallon cider vinegar to said fourth mixture,
adding about 3 quarts of hydrated magnesium sulfate to said fourth mixture,
mixing for about 10 minutes in said mixer said about 15 pounds of fine mineral powder, said about ½ gallon cider vinegar, said about 3 quarts of hydrated magnesium sulfate, and said fourth mixture thereby making said fifth mixture;

making a sixth mixture, said making a sixth mixture comprising the steps:
adding about 10 pounds of fine mineral powder selected from the group consisting of clay, hydrous aluminum silicate, and a mixture of kaolinite and quartz to said fifth mixture,
mixing said about 10 pounds of fine mineral powder and said fifth mixture until the mixture of said about 10 pounds of fine mineral powder and said fifth mixture is smooth, thereby making said sixth mixture; and making a seventh mixture, said making a seventh mixture comprising the steps:

adding about ½ gallon of cider vinegar to said sixth mixture, adding a third about 50 pounds of fine mineral powder selected from the group consisting of clay, hydrous aluminum silicate, and a mixture of kaolinite and quartz incrementally during one hour while mixing said about ½ gallon of cider vinegar and said sixth mixture, thereby making said seventh mixture.

* * * * *